(12) United States Patent
Morgan et al.

(10) Patent No.: US 6,890,548 B1
(45) Date of Patent: May 10, 2005

(54) RUMEN BYPASS SUPPLEMENT

(75) Inventors: Robert D. Morgan, Paris, IL (US); Peter A. Blagdon, Erlanger, KY (US)

(73) Assignee: Robt Morgan, Inc., Paris, IL (US)

( * ) Notice: Subject to any disclaimer, the term of this patent is extended or adjusted under 35 U.S.C. 154(b) by 241 days.

(21) Appl. No.: 10/403,718

(22) Filed: Mar. 31, 2003

Related U.S. Application Data

(60) Provisional application No. 60/380,397, filed on May 14, 2002.

(51) Int. Cl.$^7$ .......................... A23K 1/18; A23K 1/165; A61K 9/127
(52) U.S. Cl. ..................... 424/438; 424/442; 424/450
(58) Field of Search ........................................ 424/438

(56) References Cited

U.S. PATENT DOCUMENTS

| | | | |
|---|---|---|---|
| 4,160,041 A | * 7/1979 | Schroeder et al. | |
| 4,642,317 A | 2/1987 | Palmquist et al. | .......... 514/558 |
| 4,943,389 A | * 7/1990 | Weete et al. | |
| 5,182,126 A | 1/1993 | Vinci et al. | .................... 426/74 |
| 5,227,166 A | 7/1993 | Ueda et al. | ................. 424/438 |
| 5,456,927 A | * 10/1995 | Vinci et al. | |
| 5,496,571 A | 3/1996 | Blagdon et al. | ............... 426/2 |

* cited by examiner

*Primary Examiner*—Thurman K. Page
*Assistant Examiner*—R. Berko
(74) *Attorney, Agent, or Firm*—Philip L. Bateman

(57) ABSTRACT

A rumen bypass fat supplement for ruminant animals such as cattle is produced by: (a) blending about 40 to 90 parts by weight fat and about 1 to 10 parts by weight of an emulsifier; (b) adding about 5 to 20 parts by weight water to form an emulsion; (c) adding about 5 to 20 parts by weight of a Group II metal compound to the emulsion to form a reaction mixture and to initiate a salt formation reaction; (d) stirring the reaction mixture until it forms a hardened mass; (e) cooling the hardened mass to a temperature below about 100° F.; and (f) grinding the hardened mass into small particles.

18 Claims, No Drawings

RUMEN BYPASS SUPPLEMENT

CROSS-REFERENCE TO RELATED APPLICATION

This application claims the benefit of U.S. Provisional Application Ser. No. 60/380,397, filed May 14, 2002.

FIELD OF THE INVENTION

This invention relates to supplements for ruminant animals. More particularly, this invention relates to fat supplements that bypass the rumen.

BACKGROUND OF THE INVENTION

1. Ruminant Animals

Ruminant animals are mammals of the suborder *Ruminantia* that have a stomach divided into four compartments: the rumen, the reticulum, the omasum, and the abomasum. Bacteria present in the rumen enable ruminants to digest cellulosic materials such as grass. Conventional digestion occurs in the abomasum, sometimes called the "true stomach." Well-known ruminants include cattle, sheep, and goats.

A wide variety of supplements are known to improve milk production and weight gain in cattle and other ruminants. Many of these supplements are most effective only if they reach the abomasum of the animal. Unfortunately, the bacteria in the rumen are adversely affected by some of these supplements. Other supplements do not affect the rumen bacteria, but are chemically transformed or otherwise adversely affected themselves by the conditions in the rumen. Accordingly, it is common to "protect" the supplements in such a way that they bypass the rumen.

2. Fats

Fats are low cost, high energy foods that are commonly fed as supplements to cattle and other ruminants. The term "oil" is sometimes used for fats that are liquid at room temperature. The two terms are used interchangeably herein. Fats are substances of plant or animal origin that consist primarily of triglycerides. A triglyceride is produced in the condensation reaction of one molecule of glycerol with three molecules of fatty acids:

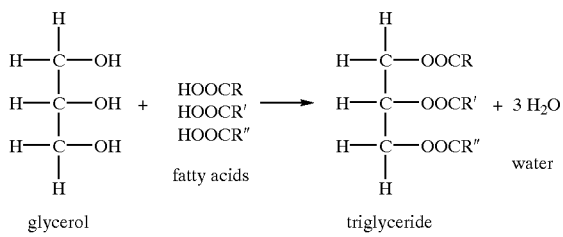

where R, R', and R" represent fatty acid radicals. A fatty acid is an aliphatic compound containing 4 to 24 carbon atoms and having a terminal carboxyl radical. Naturally occurring fats contain small quantities of other compounds, including free fatty acids and glycerol. Fats are frequently refined to remove these compounds. The term "fat" is used herein to refer to triglycerides and/or free fatty acids, as the context requires.

Naturally occurring fatty acids, with only minor exceptions, have an even number of carbon atoms and, if any unsaturation is present, the first double bond is generally located between the ninth and tenth carbon atoms. Fatty acids are sometimes abbreviated by listing their number of carbon atoms and their number of double bonds. Some of the more common fatty acids in naturally occurring fats are listed in Tables 1 and 2.

TABLE 1

SATURATED FATTY ACIDS

| Common Name | Abbreviation | Formula |
|---|---|---|
| Caprylic | 8:0 | $C_8OOH$ |
| Capric | 10:0 | $C_{10}OOH$ |
| Lauric | 12:0 | $C_{12}OOH$ |
| Myristic | 14:0 | $C_{14}OOH$ |
| Palmitic | 16:0 | $C_{16}OOH$ |
| Stearic | 18:0 | $C_{18}OOH$ |

TABLE 2

UNSATURATED FATTY ACIDS

| Common Name | Abbreviation | Formula |
|---|---|---|
| Caproleic | 10:1 | $C=C_9OOH$ |
| Lauroleic | 12:1 | $C_3=C_9OOH$ |
| Oleic | 18:1 | $C_9=C_9OOH$ |
| Linoleic | 18:2 | $C_6=C_3=C_9OOH$ |
| Linolenic | 18:3 | $C_3=C_3=C_3=C_9OOH$ |

The distribution of the different fatty acid radicals vary among naturally occurring fats. For example, the distribution of fatty acid radicals in soybean oil triglycerides is about 55% linoleic, 22% oleic, 11% palmitic, 8% linolenic, 3% stearic, and 1% other. Thus, soybean oil has an unsaturation level of about 85% (i.e., it has about 85% unsaturated fatty acids and about 15% saturated fatty acids). The distribution of free fatty acids is the same as the distribution of fatty acid radicals in the triglycerides.

Unsaturated fatty acids are known to be more digestible and are more beneficial after digestion to animals (and humans) than saturated fatty acids. An unsaturated fatty acid also has a lower melting point than a saturated fatty acid of the same number of carbon atoms. For example, animal fats have a relatively high percentage of saturated fatty acids and are typically solids at room temperature. In contrast, vegetable oils have a relatively high percentage of unsaturated fatty acids and are typically liquids at room temperature.

3. Rumen Bypass Supplements Containing Fat

Fats can adversely affect the digestion of cellulosic food in the rumen if they constitute too high a percentage of the food. It has been theorized that the adverse effect is due to several factors, including the following: (1) fats physically coat the cellulosic food which hinders the rumen bacteria in reaching the food; (2) fats, especially unsaturated fats, directly cause harm to the rumen bacteria; and (3) fats change the pH in the rumen in a way that indirectly harms the rumen bacteria.

One widely used method of increasing fat in the diet of a ruminant without adversely affecting the rumen bacteria is to include salts of fatty acids in the diet. Palmquist, U.S. Pat. No. 4,642,317, issued Feb. 10, 1987, discloses the use of calcium salts of fatty acids as a diet supplement for ruminants. The calcium salts pass through the rumen with little degradation. Accordingly, such supplements are commonly known as rumen bypasses. The calcium salts are formed by reacting fatty acids with calcium oxide (lime):

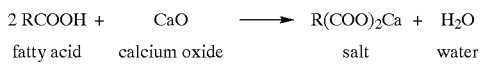

The salt formation reaction is spontaneous (no catalyst is required) and is highly exothermic (it produces heat). The reaction is typically conducted by adding a suspension of calcium oxide in water to a liquid source of fatty acids and then stirring the reaction mixture rapidly. The reaction mixture hardens as the salt is formed. The resulting product is cooled and then ground into small particles.

Theoretically, the salt formation reaction goes to completion. In other words, all the fatty acid and/or all the metal is completely reacted. However, in practice, the salt formation reaction does not go to completion. One theory is that the reaction mixture hardens before all the reactants can reach each other.

A variety of reactants are used to make rumen bypass fat supplements. Metals other than calcium, such as magnesium and other Group II elements, are suitable. However, calcium compounds are generally used because they are more readily available and less expensive. A variety of fatty acid sources are used. Preferred fatty acid sources are by-products consisting primarily of free fatty acids that are removed from naturally occurring fats. These by-products are generally less expensive than the refined fats. For example, soybean soapstock consists of free fatty acids separated from crude soybean oil. Palm fatty acid distillate consists of free fatty acids distilled from crude palm oil. Beef tallow acids are free fatty acids derived from waste beef fat.

As previously mentioned, there are nutritional benefits in using a source of fatty acids with a high percentage of unsaturation. However, because the salt formation reaction generally does not go to completion, an amount of unreacted unsaturated free fatty acids remain in the product. This creates two problems. First, the unsaturated free fatty acids have relatively low melting points and make the resulting product unacceptably soft in texture. Secondly, the unreacted fatty acids continue to slowly react after the product is produced which, in turn, creates heat. To reduce these two problems, it is common practice to add saturated fats to the reaction mixture if a fatty acid source having a high level of unsaturation is used. Accordingly, rumen bypass fat supplements typically have an unsaturation level of less than about 50%. This somewhat defeats the purpose of using a fatty acid source having a high level of unsaturation.

Vinci et al., U.S. Pat. No. 5,182,126, issued Jan. 26, 1993, discloses a rumen bypass fat supplement that contains various micronutrients. The supplement is prepared by reacting fatty acids with an alkaline earth metal compound. Vinci et al. state that optional ingredients such as antioxidants, preservatives, and surfactants can be incorporated in the process. Suitable surfactants are nonionic surfactants, hydrocolloids, and cellulose ethers.

4. Choline

Choline is a micronutrient that improves milk production due to its effect on nerve tissue and fat metabolism:

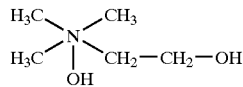

Choline also helps transition (prepartum) cattle avoid the "fatty liver" problem that can cause poor milk production and decrease fertility. Choline chloride contains a chlorine atom in place of the hydroxyl group attached to the nitrogen atom. Choline chloride has the same biological function as choline. Another choline derivative with a similar biological function is phosphatidyl choline:

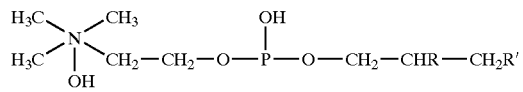

where R and R' are fatty acid groups. Crude soybean lecithin, a by-product of the soybean oil refining process that is commonly used as an emulsifier, typically contains about 15 to 20 percent phosphatidyl choline.

5. Rumen Bypass Supplements Containing Choline

Choline is rapidly metabolized by the bacteria present in the rumen. One widely used method of protecting choline is to encapsulate it in a solid fat. Blagdon et al., U.S. Pat. No. 5,496,571, issued Mar. 5, 1996, discloses a method of encapsulating choline to produce a rumen bypass supplement for ruminants. This type of encapsulation produces spherical particles having a core of choline surrounded by a shell of fat. Encapsulation is a relatively expensive manufacturing process. Furthermore, the high degree of saturation of the fat needed for solidification tends to reduce the digestibility of the choline.

Ueda et al., U.S. Pat. No. 5,227,166, issued Jul. 13, 1993, discloses a feed supplement for ruminants consisting of a coated biologically active substance, such as an amino acid, drug, or vitamin. The coating is made from a hardened oil or wax with 0.1 to 10 weight percent of an inorganic substance such as magnesium carbonate and with about 0.1 to 20 weight percent lecithin. Ueda et al. teach that the lecithin is present in the coating to provide emulsification. Ueda et al. state that the coating remains intact in the rumen but dissolves in the acidic environment of the abomasum. The amount of the inorganic substance is so small relative to the oil that little reaction occurs.

6. Rumen Bypass Supplements Containing Fat and Choline

Attempts have been made to incorporate choline into conventional rumen bypass fat supplements. However, it was discovered that choline is broken down during the conventional salt formation reaction. For example, Vinci et al. U.S. Pat. No. 5,456,927, issued Oct. 10, 1995, discloses a feed supplement for ruminants consisting of a fatty acid calcium salt containing a biologically active ingredient. Vinci et al. teach that "the selection of the biologically active ingredient is restricted because many important nutrient compounds . . . do not survive the calcium oxide hydration and fatty acid salt-formation exothermic reaction conditions which are inherent in the invention process embodiments. Nutrient compounds such as . . . choline are chemically transformed under the exothermic reaction conditions characteristic of the invention process."

Accordingly, there is a demand for an improved rumen bypass fat supplement and there is an especially great demand for one that contains both fat and choline.

SUMMARY OF THE INVENTION

One general object of this invention is to provide an improved method of producing rumen bypass fat supplements. Another general object of this invention is to provide an improved rumen bypass fat supplement. A more particular object is to provide a method of producing rumen bypass fat-choline supplements. Another more particular object is to provide a rumen bypass fat-choline supplement.

We have invented an improved method of producing a rumen bypass fat supplement for ruminant animals such as cattle. The method comprises: (a) blending about 40 to 90 parts by weight fat and about 1 to 10 parts by weight of an emulsifier; (b) adding about 5 to 20 parts by weight water to form an emulsion; (c) adding about 5 to 20 parts by weight of a Group II metal compound to the emulsion to form a reaction mixture and to initiate a salt formation reaction; (d) stirring the reaction mixture until it forms a hardened mass; (e) cooling the hardened mass to a temperature below about 100° F.; and (f) grinding the hardened mass into small particles. We have also invented an improved rumen bypass fat supplement which is produced by this method.

The rumen bypass fat supplements produced by the method of this invention have a high level of unsaturation and yet remain hard and do not heat up after production. Choline can be added to the reaction mixture and it surprisingly does not break down under the reaction conditions.

DETAILED DESCRIPTION OF THE INVENTION

1. The Invention in General

One aspect of the invention is a method of producing a rumen bypass fat supplement for dairy cattle and other ruminants. Another aspect of the invention is the supplement itself. There are four primary components that form the reaction mixture: fat, an emulsifier, water, and a Group II metal compound. A highly preferred optional component is a choline compound. Each of these components is discussed in more detail below.

2. Fat

The first component of the reaction mixture is about 40 to 90 parts by weight (pbw) fat. Suitable fats include all the naturally occurring fats from animal and vegetable sources. If the fat is solid at ambient temperature, it is heated to its melting point so it can be uniformly dispersed. The preferred fat reactant is a vegetable fat having a level of unsaturation of at least about 50%. When a fat with such a high level of unsaturation is used, the reaction product has a relatively high level of unsaturation and yet remains hard and does not heat up after production. Such fats include cottonseed oil (73% unsaturation), peanut oil (82%), soybean oil (85%), olive oil (86%), corn oil (87%), sunflower oil (89%), safflower oil (91%), and canola oil (94%). A preferred fat reactant is soybean soap stock because of its low cost and ready availability.

Soybean soap stock is a by-product of the soybean oil refining process. Oil is extracted from the soybean by solvents. After the solvent is distilled off, the crude oil is treated with water. The water hydrates the phosphatides present in crude oil, making them insoluble in the oil and enabling them to be removed by centrifugation. The phosphatides are polyhydric alcohols esterified with fatty acids and with phosphoric acid. Crude oil generally contains about one to three weight percent phosphatides. One of the phosphatides is phosphatidyl choline, also known as pure lecithin or chemical lecithin. The mixture of phosphatides removed from crude oil is sometimes known an crude lecithin or as gums. Partially refined soybean oil is commonly added back to the crude lecithin to produce a product that is flowable at room temperature. Commercial fluid soybean lecithin typically comprises about 15 to 20 weight percent phosphatidyl choline.

The degummed oil is then treated with sodium carbonate (soda ash), sodium hydroxide (caustic soda), or a mixture of alkaline components. The free fatty acids present in the oil are converted to oil-insoluble sodium soaps. These soaps are then removed and acidulated to convert them back into the free fatty acid form. They are commonly used to make commercial soaps, hence the name soap stock.

3. Emulsifier

The second component of the reaction mixture is an emulsifier. The emulsifier is added in an amount sufficient to form an emulsion when the water component is added. This amount depends on the emulsifier, the amount of water which will be added, and other factors. The amount is generally about 1 to 10 parts by weight. The emulsifier is thoroughly blended with the fat. The emulsifier enables an emulsion to be formed when water is added. The emulsion allows more intimate contact between the reactants and enables the reaction to go further to completion. Thus, more of the fat is converted to a form which passes through the rumen with minimal effect on the rumen bacteria. Suitable emulsifiers include soybean lecithin, glyceryl monostearate, other fatty acid esters of polyhydric alcohols with at least one free hydroxyl group, and the like. A preferred emulsifier is fluid soybean lecithin because of its low cost and ready availability. Fluid soybean lecithin is also preferred because it provides choline. The production of fluid soybean lecithin is discussed in detail above.

4. Water

The third component of the reaction mixture is about 5 to 20 parts by weight water. The presence of the emulsifier enables a water-in-oil emulsion to be formed. An emulsion is a stable mixture of two or more immiscible liquids held in suspension by emulsifiers. In a water-in-oil emulsion, the oil (fat) is the continuous phase and the water is the disperse phase. The water provides two benefits to the reaction. First, it increases the rate and degree of completion of the reaction by increasing the mobility of the metal ions. Second, It provides a heat sink that absorbs the heat generated by the reaction. The water is present before the salt formation reaction begins. It can be added to the fat-emulsifier blend before the Group II metal compound. However, it is preferably first added to the Group II metal compound and then the Group II metal compound-water slurry is added to the fat-emulsifier blend.

5. Group II Metal Compound

The fourth component in the reaction mixture is about 5 to 20 parts by weight of a Group II metal compound. The preferred Group II metal compounds are calcium and magnesium compounds such as oxides, hydroxides, carbonates, phosphates, and the like. The most preferred Group II metal compounds are calcium oxide (lime) and calcium hydroxide (quicklime). The Group II metal compound is preferably added in a stoichiometric quantity. As discussed above, the Group II metal compound is preferably suspended in water before being added to the fat-emulsifier blend. Accordingly, the reaction mixture is preferably created by first blending the fat with the emulsifier, then suspending the Group II metal compound in water, and then combining the two liquids.

6. Choline Compound

An optional, but highly preferred, component is about 1 to 20 parts by weight of a choline compound. The amount of choline added depends on the desired level of choline in the final product. Suitable choline compounds include choline itself and its derivatives which have a similar biological function, including choline chloride and phosphatidyl choline. As discussed above, fluid soybean lecithin is an emulsifier which also contains about 15 to 20 weight percent phosphatidyl choline. Using choline chloride as a source of choline enables higher levels of choline to be achieved in the final product. The choline is surprisingly not broken down during the salt formation reaction and, furthermore, is not broken down in the rumen when ingested by a ruminant.

7. Other Optional Components

A variety of other optional components may be added to the reaction blend. For example, adding a small quantity of tertiary butyl hydroquinone (TBHQ) as an anti-oxidant to reduce the danger of fire is often desirable. As another example, when fluid soybean lecithin is used as an emulsifier and as a source of choline, the non-phosphatidyl choline components of the fluid soybean lecithin are present in the reaction blend.

8. Salt Formation Reaction

The highly exothermic salt formation reaction occurs spontaneously as soon as the Group II metal compound contacts the fat. The reaction mixture is preferably stirred to promote contact between the reactants before the reaction products harden into a mass.

9. Cooling and Grinding

After the reaction has completed, the hardened mass is cooled to a temperature below about 100° F. The hardened mass is then ground into the desired size using conventional equipment such as hammer mills, attrition mills, or the like.

10. Use of the Supplement

The rumen bypass fat supplement produced by the method of this invention is especially beneficial to dairy cattle and other ruminants. Dairy cattle at any point in the lactation cycle benefit from the supplement. The supplement passes through the rumen with minimal degradation. The supplement is preferably added to the diet of dairy cattle in an amount of sufficient to create a more positive energy balance in the animal.

EXAMPLES

The following examples are illustrative only.

Example 1

This example illustrates a control in which no emulsifier is used.

Two thousand eight hundred eighty-six (2886) parts by weight (pbw) of crude vegetable fatty acids (over 90% free fatty acids) were mixed with 1.5 pbw of tertiary butyl hydroquinone (TBHQ) and then blended with 300 pbw of quicklime (Ca(OH)$_2$) suspended in 300 pbw of water. The reaction was sudden and exothermic. The resultant mass was cooled and crushed. After crushing the particles were soft and sticky. The product was packaged in multi-walled paper bags. After two weeks of storage some of the bags began to "heat" with liberation of smoke and charring of the material. Material in the mass that was not actually charred was softened or melted to the point that it was unusable in animal feed.

Example 2

This example illustrates the production of a rumen bypass fat supplement using glyceryl mono-stearate as an emulsifier.

Two thousand eight hundred fifty-four (2854) pbw of hot crude vegetable fatty acids (over 90% free fatty acids) were mixed with 32 pbw of glyceryl mono-stearate and 1.5 pbw of TBHQ. The temperature of the fatty acids was only hot enough to melt the glyceryl mono-stearate so that it could be intimately mixed with the fatty acids. The mixture was in turn mixed with 300 pbw of quicklime (Ca(OH)$_2$) suspended in 300 pbw of water. The reaction was sudden and exothermic. The resultant mass was cooled and crushed. After crushing the particles were hard and free flowing. The product was packaged in multi-walled paper bags and stacked on a pallet. After 2 weeks the product was cool and free flowing.

Example 3

This example illustrates the production of a rumen bypass fat supplement using fluid soybean lecithin as an emulsifier and as a source of choline.

Two thousand seven hundred eighty-six (2786) pbw of crude vegetable fatty acids (over 90% free fatty acids) were mixed with 100 pbw of fluid soybean lecithin and 1.5 pbw of TBHQ. This mixture was in turn mixed with 300 pbw of quicklime (Ca(OH)$_2$) suspended in 300 pbw of water. Again the reaction was sudden and exothermic. The resultant mass was cooled and crushed. After crushing the particles were hard and free flowing. The product was packaged in multi-walled paper bags and stacked on a pallet. After two weeks the material showed no sign of heating and was still free flowing.

Example 4

This example illustrates the production of a rumen bypass fat-choline supplement using fluid soybean lecithin as an emulsifier and as a source of choline.

One thousand and twenty (1020) pbw of soybean acidulated soap stock with an acid value of approximately 180 is blended with 980 pounds of fluid soybean lecithin and one pound of ethoxyquin antioxidant. This mixture is heated to approximately 200° F. and then 100 pounds of water is added. Finally the entire mixture is reacted with 381 pounds of hydrated lime. The reaction is vigorously exothermic and forms a hard mass. This mass is in turn cooled and ground to appropriate size for use in feed.

The finished product contains approximately 6% phosphatidyl choline in a form that the rumen bacteria cannot degrade. Use of slightly over one-half pound of this finished product supplies a ruminant with 15 grams of phosphatidyl choline, which is sufficient to increase milk production and also to prevent other diseases such as fatty liver and displaced uterus.

In addition, the mixture supplies 78% dietary fat with a high percentage of unsaturated fatty acids which are very desirable in the ruminant diet. The lecithin also improves the digestibility of the fat.

Example 5

This example illustrates the production of a rumen bypass fat-choline supplement using fluid soybean lecithin as an emulsifier and as a source of choline and using choline chloride as an additional source of choline.

One thousand four hundred eighty (1480) pounds of crude vegetable fatty acids (over 90% free fatty acids) were blended with 60 pounds of fluid soybean lecithin. Three hundred fifty-four (354) pounds of a 70% aqueous solution of choline chloride were then added to the blend. The temperature of the blend was maintained at least about 130° F. so that the cooling effects of the lecithin and the choline chloride solution did not congeal the mixture. Strong agitation was needed to form a water-in-oil emulsion, but once formed the emulsion was relatively stable.

The emulsion was then reacted with 200 pounds quicklime suspended in 200 pounds water. The reaction proceeded quickly without any catalysis. After the reaction was completed, the mass was cooled and crushed. Analysis of the product showed that it contained 12.5% choline chloride, indicating that little or no degradation of choline occurred.

We claim:

1. A method of producing a rumen bypass fat and choline supplement, the method comprising:
   (a) blending about 40 to 90 parts by weight fat, about 1 to 10 parts by weight of an emulsifier, selected from the group consisting of soybean lecithin and fatty acid esters of polyhydric alcohols with at least one free hydroxyl group and a sufficient quantity of a choline compound such that the blend contains about 1 to 20 parts by weight of choline compound;
   (b) adding about 5 to 20 parts by weight water to form an emulsion;
   (c) adding about 5 to 20 parts by weight of a Group II metal compound to the emulsion to form a reaction mixture and to initiate a salt formation reaction;
   (d) stirring the reaction mixture until it forms a hardened mass;
   (e) cooling the hardened mass to a temperature below about 100° F.; and
   (f) grinding the hardened mass into small particles.

2. The method of claim 1 wherein the fat has a level of unsaturation of at least about 50%.

3. The method of claim 2 wherein the water and the Group II metal compound are mixed together before being added to the blend.

4. The method of claim 3 wherein the Group II metal compound is a calcium compound.

5. The method of claim 4 wherein the calcium compound is added in about a stoichiometric amount.

6. The method of claim 5 wherein the fat consists essentially of fatty acids.

7. The method of claim 6 wherein the choline compound comprises choline chloride or phosphatidyl choline.

8. The method of claim 7 wherein the emulsifier comprises soybean lecithin.

9. The method of claim 8 wherein the choline compound consists essentially of phosphatidyl choline present in the soybean lecithin.

10. A rumen bypass fat and choline supplement for ruminant animals, the supplement comprising the product produced by a method comprising:
    (a) blending about 40 to 90 parts by weight fat, about 1 to 10 parts by weight of an emulsifier, selected from the group consisting of soybean lecithin and fatty acid esters of polyhydric alcohols with at least one free hydroxyl group and a sufficient quantity of a choline compound such that the blend contains about 1 to 20 parts by weight of choline compound;
    (b) adding about 5 to 20 parts by weight water to form an emulsion;
    (c) adding about 5 to 20 parts by weight of a Group II metal compound to the emulsion to form a reaction mixture and to initiate a salt formation reaction;
    (d) stirring the reaction mixture until it forms a hardened mass;
    (e) cooling the hardened mass to a temperature below about 100° F.; and
    (f) grinding the hardened mass into small particles.

11. The supplement of claim 10 wherein the fat has a level of unsaturation of at least about 50%.

12. The supplement of claim 11 wherein the water and the Group II metal compound are mixed together before being added to the blend.

13. The supplement of claim 12 wherein the Group II metal compound is a calcium compound.

14. The supplement of claim 13 wherein the calcium compound is added in about a stoichiometric amount.

15. The supplement of claim 14 wherein the fat consists essentially of fatty acids.

16. The method of claim 15 wherein the choline compound comprises choline chloride or phosphatidyl choline.

17. The supplement of claim 16 wherein the emulsifier comprises soybean lecithin.

18. The supplement of claim 17 wherein the choline compound consists essentially of phosphatidyl choline present in the soybean lecithin.

* * * * *